(12) United States Patent
Fox

(10) Patent No.: US 10,695,114 B2
(45) Date of Patent: Jun. 30, 2020

(54) METHOD FOR FORCE, DISPLACEMENT, AND RATE CONTROL OF SHAPED MEMORY MATERIAL IMPLANTS

(71) Applicant: William Casey Fox, Pipe Creek, TX (US)

(72) Inventor: William Casey Fox, Pipe Creek, TX (US)

(73) Assignee: William Casey Fox, Pipe Creek, TX (US)

( * ) Notice: Subject to any disclaimer, the term of this patent is extended or adjusted under 35 U.S.C. 154(b) by 130 days.

(21) Appl. No.: 16/102,240

(22) Filed: Aug. 13, 2018

(65) Prior Publication Data

US 2018/0360507 A1 Dec. 20, 2018

Related U.S. Application Data

(60) Division of application No. 15/179,730, filed on Jun. 10, 2016, now abandoned, which is a continuation of
(Continued)

(51) Int. Cl.
| | |
|---|---|
| *A61B 17/80* | (2006.01) |
| *A61B 17/064* | (2006.01) |
| *A61B 17/122* | (2006.01) |
| *A61F 2/82* | (2013.01) |
| *A61F 6/14* | (2006.01) |
| *A61B 17/00* | (2006.01) |
| *A61B 17/68* | (2006.01) |

(Continued)

(52) U.S. Cl.
CPC .......... *A61B 17/809* (2013.01); *A61B 17/064* (2013.01); *A61B 17/0642* (2013.01); *A61B 17/122* (2013.01); *A61B 17/68* (2013.01); *A61F 2/01* (2013.01); *A61F 2/82* (2013.01); *A61F 6/14* (2013.01); *A61B 2017/00084* (2013.01); *A61B 2017/00867* (2013.01); *A61B 2090/064* (2016.02); *A61F 2002/30092* (2013.01); *A61F 2002/482* (2013.01); *A61F 2210/0033* (2013.01)

(58) Field of Classification Search
CPC . A61B 17/809; A61B 17/064; A61B 17/0642; A61B 2017/00867
See application file for complete search history.

(56) References Cited

U.S. PATENT DOCUMENTS

| | | | | |
|---|---|---|---|---|
| 3,786,806 | A * | 1/1974 | Johnson | ................ A61L 31/022 606/78 |
| 3,786,814 | A * | 1/1974 | Armao | ................... A61B 18/02 606/23 |

(Continued)

*Primary Examiner* — Christian A Sevilla
(74) *Attorney, Agent, or Firm* — Dickinson Wright PLLC; Ross Spencer Garsson

(57) ABSTRACT

A method for force, displacement, and rate control of shape memory material implant. The rate of implant shape change as well as the force exerted on the surrounding tissue of the implant can be controlled by the surgeon and the extent of movement is controlled in circumstances where the bone element is free to move. The invention allows for the first time the fine control of force when fixating osteoporotic bone and rate of bone transport when working near the spinal cord. This heating profile of the implant provides the surgeon to control the extent of microstructure phase transformation so that the rate, force or extent of tissue movement can be controlled individually or together.

21 Claims, 9 Drawing Sheets

Related U.S. Application Data application No. 11/804,294, filed on May 17, 2007, now abandoned, which is a division of application No. 10/356,830, filed on Feb. 3, 2003, now Pat. No. 7,240,677.

(51) Int. Cl.
*A61F 2/01* (2006.01)
*A61F 2/48* (2006.01)
*A61B 90/00* (2016.01)
*A61F 2/30* (2006.01)

(56) References Cited

U.S. PATENT DOCUMENTS

| | | | | |
|---|---|---|---|---|
| 3,868,956 | A * | 3/1975 | Alfidi | A61B 17/22 606/194 |
| 4,485,816 | A * | 12/1984 | Krumme | A61B 17/0644 606/219 |
| 5,002,563 | A * | 3/1991 | Pyka | A61B 17/0644 606/222 |
| 5,190,546 | A * | 3/1993 | Jervis | A61B 17/0642 606/78 |
| 5,246,443 | A * | 9/1993 | Mai | A61B 17/0644 606/78 |
| 5,290,289 | A * | 3/1994 | Sanders | A61B 17/7002 606/279 |
| 5,397,331 | A * | 3/1995 | Himpens | A61B 17/0057 606/151 |
| 5,474,557 | A * | 12/1995 | Mai | A61B 17/0642 606/219 |
| 5,617,854 | A * | 4/1997 | Munsif | A61B 18/1492 600/374 |
| 5,779,707 | A * | 7/1998 | Bertholet | A61B 17/8004 606/75 |
| 5,964,770 | A * | 10/1999 | Flomenblit | C22F 1/006 606/78 |
| 5,989,268 | A * | 11/1999 | Pugsley, Jr. | A61B 17/064 606/144 |
| 6,063,111 | A * | 5/2000 | Hieshima | A61B 17/12022 606/191 |
| 6,200,330 | B1 * | 3/2001 | Benderev | A61B 17/0401 411/358 |
| 6,325,805 | B1 * | 12/2001 | Ogilvie | A61B 17/70 606/75 |
| 6,336,928 | B1 * | 1/2002 | Guerin | A61B 17/7059 606/282 |
| 6,348,064 | B1 * | 2/2002 | Kanner | A61B 17/0057 411/457 |
| 6,494,889 | B1 * | 12/2002 | Fleischman | A61B 17/064 606/153 |
| 7,240,677 | B2 * | 7/2007 | Fox | A61F 2/01 128/897 |
| 2001/0018592 | A1 * | 8/2001 | Schaller | A61B 17/0469 606/151 |
| 2002/0007184 | A1 * | 1/2002 | Ogilvie | A61B 17/0642 606/248 |
| 2002/0029044 | A1 * | 3/2002 | Monassevitch | A61B 17/0642 606/75 |
| 2002/0087175 | A1 * | 7/2002 | Gifford, III | A61B 17/064 606/153 |
| 2003/0074075 | A1 * | 4/2003 | Thomas, Jr. | A61F 2/442 623/17.16 |
| 2004/0172107 | A1 * | 9/2004 | Fox | A61F 2/01 607/96 |
| 2017/0007305 | A1 * | 1/2017 | Hollis | A61B 17/8057 |

* cited by examiner

| Power Setting for Percentage of Maximum Closing Force Over a Selected Period | | | | | | | | | | |
|---|---|---|---|---|---|---|---|---|---|---|
| Implant Type: Cervical Plate | | | | | | | | | | |
| Force (%) | 10 | 20 | 30 | 40 | 50 | 60 | 70 | 80 | 90 | 100 |
| Time | | | | | | | | | | |
| 1 | 1 | 2 | 3 | 4 | 5 | 6 | 7 | 8 | 9 | 10 |
| 2 | | 1 | 2 | 3 | 4 | 5 | 6 | 7 | 8 | 9 |
| 3 | | | 1 | 2 | 3 | 4 | 5 | 6 | 7 | 8 |
| 4 | | | | 1 | 2 | 3 | 4 | 5 | 6 | 7 |
| 5 | | | | | 1 | 2 | 3 | 4 | 5 | 6 |
| 6 | | | | | | 1 | 2 | 3 | 4 | 5 |
| 7 | | | | | | | 1 | 2 | 3 | 4 |
| 8 | | | | | | | | 1 | 2 | 3 |
| 9 | | | | | | | | | 1 | 2 |
| 10 | | | | | | | | | | 1 |

Fig. 5

METHOD FOR FORCE, DISPLACEMENT, AND RATE CONTROL OF SHAPED MEMORY MATERIAL IMPLANTS

CROSS-REFERENCE TO RELATED APPLICATION

This Application is a divisional application of U.S. patent application Ser. No. 15/179,730, filed Jun. 10, 2016, entitled "Force, Displacement, And Rate Controlled Shape Memory Material Implants, which is a continuation application of U.S. patent application Ser. No. 11/804,294, filed on May 17, 2007, entitled "System And Method For Force, Displacement, And Rate Control Of Shaped Memory Material Implants," which is a divisional of U.S. patent Ser. No. 10/356,830, filed on Feb. 3, 2003, now known as U.S. Pat. No. 7,240,677, issued on Jul. 10, 2007, and entitled "System And Method For Force, Displacement, And Rate Control Of Shaped Memory Material Implants."

FIELD OF THE INVENTION

The present invention relates to instrumentation and a method of controlling in vivo shape changes in devices formed from memory materials that change shape when heated. In particular, the present invention relates to surgical instrumentation, used to control the rate of shape change and forces imparted to the surrounding tissue by memory material implants during medical use.

BACKGROUND-DISCUSSION OF THE PRIOR ART

Shape memory alloys such as nitinol have been well known since their development by Buehler and Wiley (U.S. Pat. No. 3,174,851) in 1965. Other metals, such as AuCd, $FePt_3$, beta Brass and InTI, exhibit shape memory behavior. These materials have the property of changing shape in response to a change in material temperature. This shape change potential is imparted into the memory metal device through a series of heat treatments.

The transition temperature range is imparted to the material through varying mixtures of intermetallic compounds such as nickel-titanium and heat treatment. The heat treatment methods for the material generally consist of at a minimum high temperature setting of the desired final shape of a device followed by a low temperature straining of the device to a second shape. Then when the device in the second shape and brought to the transition temperature the device returns to the preprogrammed final shape. The shape change occurs due to the transition of the material from a martensitic to austenitic phase microstructure. These heat-initiated changes cause gross changes in the shape of the implant formed from the memory metal.

Shape memory alloys have been used for a wide range of industrial and medical applications. Medical applications include but are not limited to: catheter, intrauterine contraceptive device, gastrointestinal compression-dip, blood vessel filter, coronary artery stent, skin staple, bone staple, and bone plate.

In the prior art memory metal implants have been caused to change shape by heating by their environment, applied current or directed energy. Implants and surgical instruments that change shape in the environment of human body temperature have been described by Jervis and include but are not limited to laprascopic instruments, needle and suture manipulation devices, and expansion and shrinkable coil stents and closures. Implants, that change shape using the Joule effect through resistive heating, have been described by Krumme, Alfidi and Flot. The prior art associated with resistive heating of memory alloys have not recognized the need for the control of the rate of shape change and magnitude of forces applied by the implant to the surrounding tissue. Furthermore, the prior art describes the full transition of the material, from martensitic to austinetic microstructure through the delivery of either: 1) a predetermined amount of heat energy to a specific implant (Flot), 2) opening to an initial configuration (Alfidi) or 3) until the shape change breaks contact with current carrying electrodes (Krumme).

Only Jervis recognized the need for force and shape control of a musculoskeletal implant but controlled these through a mechanical actuator that resisted the heat induced shape change. This approach was required due to the transition temperature of the metal fully converting to the austinetic phase at body temperature. In this case, there was no force control of the implant due to the body temperature transition point of the metal, which resulted in the implant applying the maximum potential force to the surrounding tissue.

The prior art is at a significant disadvantage to the subject invention in the field of orthopaedics due to the lack of a method and system to control the rate and maximum shape change force exerted on the surrounding tissue. The clear advantages of the subject invention will be seen in the following review of the prior art.

Methods of heating memory alloy medical devices to change their shape include: conductive heat transfer (Alfidi [U.S. Pat. No. 3,868,956] and Krumme [U.S. Pat. Nos. 4,550,870 and 4,485,816]), electromagnetic energy heating, and resistive heating using the joule effect (Alfidi [U.S. Pat. No. 3,868,956], Krumme [U.S. Pat. No. 4,485,816] and Flot [U.S. Pat. No. 6,268,589 B1 and U.S. Pat. No. 6,323,461 B2]). One source of conductive heat energy is the ambient temperature of the human body (Jervis: U.S. Pat. Nos. 4,665,906, 5,067,957, 5,190,546, and 5,597,378).

Resistive heating has been found to be a convenient method for medical devices. Resistive heating devices have used both AC current (Flot [U.S. Pat. No. 6,268,589 B1]) and DC current (Alfidi [U.S. Pat. No. 3,868,956] and Krumme [U.S. Pat. No. 4,485,816]) to change the implant shape. These systems. control the heating current so as to limit the maximum temperature (Flot [U.S. Pat. No. 6,268, 589 B1]) and (Alfidi [U.S. Pat. No. 3,868,956]) or extent of shape change of the implant (Krumme [U.S. Pat. No. 4,485,816] and Alfidi [U.S. Pat. No. 3,868,956]). Though these methods and devices control thermal injury to tissue and extent of shape change they are significantly limited in musculoskeletal applications.

Krumme (U.S. Pat. No. 4,485,816; col 6, ln 37-44) controls the maximum temperature and extent of shape change by causing contact between the implant and electrode to break as a result of the shape change. This simultaneous secession of heat or electrical energy flow limits heating of the implant to a level that makes it suitable for use in implant applications. This implant heating strategy results in a predetermined degree of shape change but no control of its force or rate of shape change. This strategy significantly limits implant design because in many musculoskeletal uses solid stable bone structures may not allow the implant to change shape only to provide compressive forces. Thus in this application the shape change would not break contact between the implant and electrode and stop heat energy delivered. Thus the heating device of Krumme can not control either rate of shape change or force exerted on the surrounding tissue.

Alfidi [U.S. Pat. No. 3,868,956, col 7, ln 20-33] provided time and voltage controls to limit the energy applied to an implant so as to control the extent of its shape change at temperatures compatible with the enclosure of the heating element and the biologic environment in which the implant is used. Alfidi could monitor the actual current flow over a fixed preset time. Alfidi heated quickly to avoid thermal damage [U.S. Pat. No. 3,868,956, col 3, ln 41-43] and expand the "wire appliance to a desired degree". [U.S. Pat. No. 3,868,956, col 3, ln 10-15] where desired degree was consistently referenced as "it assumes . . . a configuration . . . which . . . is . . . substantially similar to said initial configuration." [U.S. Pat. No. 3,868,956, col 8, ln 61-63]. Where the initial configuration is the first shape referenced above that is formed during the initial high-temperature heat treatment. Thus the heating device of Alfidi can not control force exerted on the surrounding tissue.

Flot [U.S. Pat. No. 6,268,589 B1 col 1, ln 44-47] provided voltage control but removed control of the energy delivery time described by Alfidi [U.S. Pat. No. 3,868,956] from the surgeon to lessen the potential for overheating the implant and causing tissue injury. Flot matched an implant size to a specific voltage setting for a fixed period of time through the use of resistor (R17) on the circuit board [U.S. Pat. No. 6,268,589 B1 col 3, ln 21-23]. This matching of implant to voltage required to provide the complete martensitic to austenitic of an implant is proposed by Flot to be matched to an implant mass so that it does not reach a temperature sufficiently high so as to cause thermal necrosis to surrounding tissue. Flot's approach is limiting in that without control of time the range of implants mass that can be effected with this invention is, limited to 0.8 grams to 2.8 grams [U.S. Pat. No. 6,268,589 B1 col 3, ln 3-7 and col 4, ln 37-39]. This occurs due to the implant's heating profile being dependent only on applied voltage magnitude and the impedance and mass of the implant. Without user control of both the time and applied voltage the total heating energy to an implant is limited. Thus the implant sizes that can be heated through their transition temperature is limited. The fixed relationship between implant size and control settings presented by Rot teaches against the control of forces exerted by the shape memory alloy implant on the surrounding tissue. Furthermore the inability to control heat energy delivery time teaches away from controlling the rate of memory-metal-implant shape changes so as to protect vital structures.

Jervis, [U.S. Pat. No. 4,665,906 example II and IV] whose medical shape memory allow implants have a transition temperature substantially at body temperature is the only author of the prior art that realizes the importance of controlling the rate and force applied by the shape changing memory alloy implant. Due to the full transition of martensitic to austenitic microstructure occurring in the implant at body temperature, Jervis controls the shape change with a "mechanical restraint . . . achieving excellent force and time control, and permitting the surgeon to make adjustments as desired." The advantage of not requiring a separate instrument to control the closure of the implant through applied heat energy is greatly overcome by the need for a "mechanical restraint" instrument. This instrument limits the use of the shape memory implant. In medicine a different instrument would be needed for each implant design. Furthermore, many uses would not be realized due to the bulk and functional requirements of the instrument needed to control the closing force and rate of the implant. Finally, once placed and the mechanical restraint removed the implant fully converts to the austinetic microstructure and there is no longer any force control. Thus the invention of Jervis has significant disadvantages compared with the subject invention.

The prior art consistently teaches an instrument or techniques to transform the implant to a single final state. The art describes high temperature setting of an initial shape, low temperature deformation to a second shape state, and heating, of the implant to return the implant to its initial shape. The prior art does not present, as the subject invention describes, a device or method to control the martensitic to austinetic transformation so that a plurality of fixation forces and rates can be achieved from each of a plurality of implant designs. Jervis's implant reaches the state associated with body temperature heating. Krumme reaches the state associated with shape change breaking contact with the current source. Alfidi reaches a configuration that is substantially similar to said initial configuration. Flot provides "predetermined quantities of heat, each corresponding to a given size of clamp" but does not provide a plurality of heat energies to a single style clamp to control the force applied to bone or its rate of closure.

These limitations of the prior art have caused memory metals to be limited in use in orthopaedics. Memory alloy implants have found use as simple two and four leg staples but have not reached the potential of implants that can be manipulated with precise control to change their shape and move bony structures. The lack of surgeon control of forces applied to bone is of significant concern in osteoporotic bone and thus with implants and heat energy sources described in the prior art. Furthermore the quick shape changing movement of implant and bony structures described under the prior art could pinch and injury the spinal cord. This inability to adjust the implants shape-changing response within the martensitic to austenitic transformation temperature range to control its force and closure rate has discouraged the clinical use of these systems. The subject invention presents an innovative solution to these clinical issues Objects and Advantages The subject invention for musculoskeletal implant applications recognizes that closing force and rate of shape change of the implant are critical factors in the implants' success due to the wide range of bone strength, anatomical variation and medical need.

In osteoporotic bone an implant that closes with too much force may create fracture. In displaced fractures of healthy bone, implant forces exerted by its shape change may be too low to pull the fracture line closed. If the forces are just right, bone is stimulated to gain mass and strengthen. This tendency of bone to adapt to the loads applied to it is described by Wolff's Law. Implants that allow the surgeon to control these forces provide unique clinical benefit in stabilizing bone fractures and applying residual forces that take advantage of Wolff s Law and advance bone healing. The lack of control, of the peak and residual forces by the inventions of the prior art, has significantly impeded the adoption of musculoskeletal implants that changed shape.

A secondary but significant element of this invention is the ability for the surgeon to control the rate of shape change of the memory metal. In the fixation of bone, memory metals when heated move bone to close fracture lines or joints intended to be fused. When working in the spine the movement of vertebra to bring them into apposition to facilitate fusion should be done slowly so as to not cause impingement of the spinal cord. When heating orthopaedic memory metal implants that change the relative position or angle of bone, it must be done slowly so as to achieve the proper position. The novel feature of controlling the rate of movement of members of bone fixation implants provides the surgeon new treatment modalities and opens new design possibilities heretofore not available.

Implants may have multiple members that change shape. Some of these members may be controlled individually and others may need to be controlled together. These multi-member heating strategies may be accomplished by separately heating each member or through the use of multi-conductor electrodes that heat select areas of the implant and heat transfer models of the implant to estimate the overall heating profile of each implant region. The controller using, its model, lookup-table or feedback control or direct measurement of the implant temperature will allow the surgeon to plan the fixation strategy so as to optimize the biomechanical construct for each unique bone fixation condition.

The subject invention controls maximum force and rate of implant change through fine control of the total heat energy applied to the implant. The system can also control the extent of opening in the few musculoskeletal indications where bone transport occurs and there is little or no tissue force. Algorithms, numerical or graphical models, lookup table of settings or measurements of implant temperature and extent of shape change, combined with a current source will give the surgeon the control necessary to utilize memory alloy implants to their full potential for musculoskeletal reconstruction.

For the first time the subject invention provides force and shape change rate control through controlling the implant temperature so that it is within the temperature range which the martensitic to austenitic transformation occurs for a given implant composition. Through controlling the extent of the material's transformation the subject invention is able to control the implants applied force, rate of closure, and extent of closure together or separately while maintaining the surface temperature at a level that will not cause thermal necrosis of the surrounding tissue.

This novel approach to controlling the implant for the first time allows the surgeon to program a implant to provide a range of forces or closing rates so as to meet the clinical requirements. This allows the surgeon to adjust the implant once placed in the body to get the required musculoskeletal effect.

Accordingly, several objects and advantages of this invention are herein described: 1) controls the rate of shape change of memory alloy devices, 2) controls the compression or distraction forces between bones, 3) provides control on the relative positions of bones and angular changes in multiple bone structures, 4) controls implant heating profiles through a lookup table which contains at a minimum force, rate and implant model information and 5) controls implant heating profiles through measurement of the temperature of the staple and using this information in a feedback control loop set to a defined rate and force. These objects and advantages are achieved in addition to the features of other inventions that limit the temperature of the implant to a level below that which will cause tissue death. Further objects and advantages of the subject invention will become apparent from a consideration of the drawings and ensuing description.

SUMMARY OF THE INVENTION

The subject invention is a system to control the surgical heating of an implant formed from memory metal so as to control its rate of shape change and the forces it exerts on surrounding bone or in bone transport the extent of bone movement. These variables will be controlled while keeping the implant's surface temperature clinically below the point of thermal necrosis of tissue. The invention consists of an electrode and electrical console that contacts the implant at a plurality of locations and delivers to each location a selected amount of heat energy over a selected period of time. This allows the surgeon to slowly close an implant or an implant element and optimize bone fixation and position.

The subject invention accounts for the variables associated with the shape changing heat response of the memory metal implant to heat energy such as resistive heat (electrical current flow), conductive heat (contact heating element), inductive heat (such as electromagnetic or microwave). The primary variables which cause a certain implant temperature and shape change response are: 1) magnitude of energy flow, 2) duration energy of flow, 3) mass of the implant, 4) shape of the implant, 5) initial state of the implant, 6) impedance of the implant, 7) thermal stability of the implant and 8) environment of the implant. The subject invention through a mathematical model, family of lookup tables or direct measurement of the temperature uses a current source and user defined inputs to controls the implant kinematics of shape change.

BRIEF DESCRIPTION OF THE DRAWINGS

Further objects and advantages of this invention will become apparent from consideration of the drawings and ensuing description of the preferred embodiment.

FIG. 5 Lookup table example

LIST OF REFERENCE NUMERALS

Figure 7:
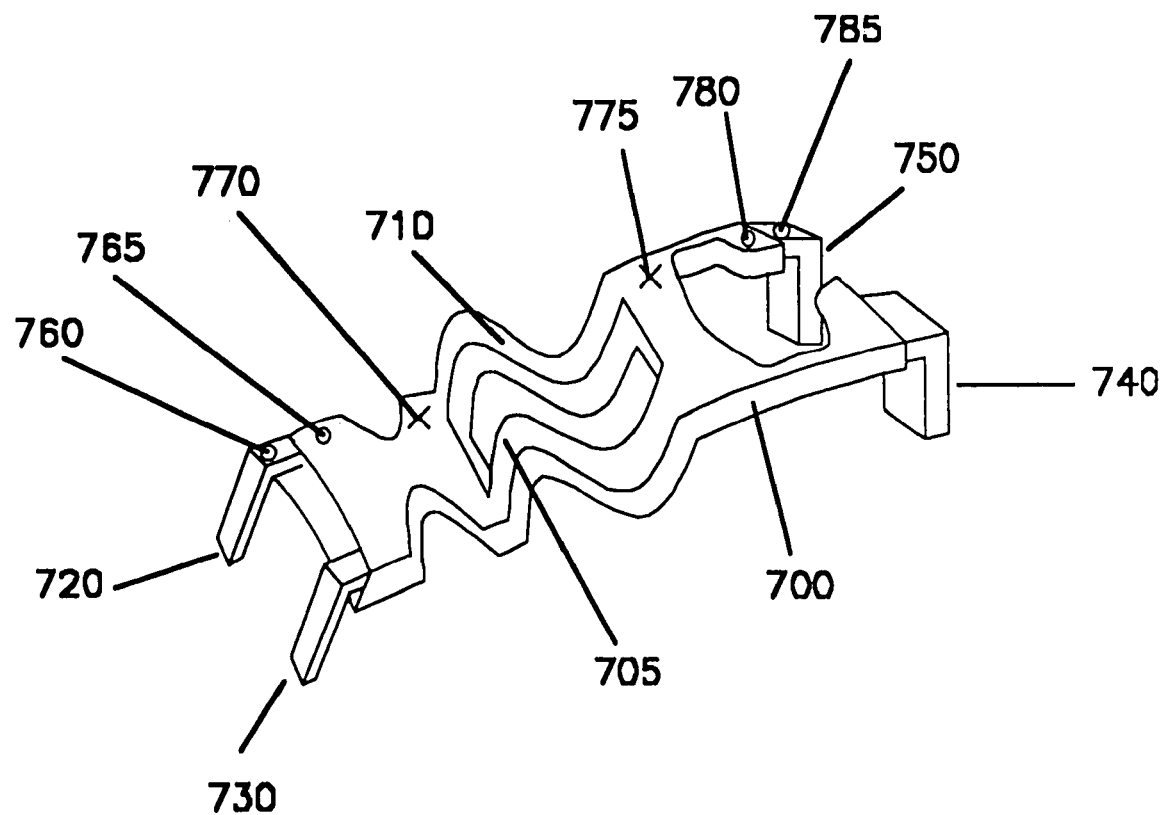
FIG. 7 Multi-element implant example

100 Two second heating curve for martensitic to austinetic phase transformation
110 Ten second heating curve for martensitic to austinetic phase transformation
200 Austinetic transformation start temperature and inflection in force curve
210 Austinetic transformation end temperature
220 Minimum tissue force seen at body temperature
230 Maximum tissue force seen at body temperature
300 Force versus time curve while heating
400 Power supply with isolation transformer
410 AC to DC power converter
420 User set timer circuit
430 User set power circuit
440 Current delivery electrode
450 Circuit board
460 Electrode conductor to implant
470 Heating control button
475 Implant-system continuity light 480 Implant-system heat energy light
485 Lookup table
490 Front control panel with time, power, on-off switch, and indicator lights
495 Audible operational indicator
500 Implant force and rate control lookup table
510 Heating duration data
520 Force level data
530 Power level within cells of the lookup table
600 Power supply with isolation transformer
610 AC to DC power converter
620 Timer circuit
630 Front panel control with keyboard and monitor
640 Current delivery electrode
650 Microprocessor running model, algorithm or sorting the lookup table
655 Circuit board
660 Audible operational indicator
670 Power circuit
680 Electrode handle
685 Electrode start button
690 Implant-system continuity light and heat energy light combined
695 Electrode conductor to implant
700 Spinal plate
705 First length or angle shape-changing member
710 Second length or angle shape-changing member
720 First bone anchoring shape-changing member
730 Second bone anchoring shape-changing member
740 Third bone anchoring shape-changing member
750 Fourth bone anchoring shape-changing member
760 First electrode contact point for member 720
765 Second electrode contact point for member 720
770 First electrode contact point for member 710
775 Second electrode contact point for member 710
780 First electrode contact point for member 750
785 Second electrode contact point for member 750
800 First electrode element for FIG. 7 member 720
810 First electrode element for FIG. 7 member 730
820 First electrode element for FIG. 7 member 740
830 First electrode element for FIG. 7 member 750
840 Second electrode element for FIG. 7 member 740
850 Second electrode element for FIG. 7 member 730
860 Second electrode element for FIG. 7 member 720
870 Second electrode element for FIG. 7 member 750
880 Multi-electrode handle
890 Electrode conductor bundle
895 Individual electrode conductors
900 Power supply
910 User operated switch
920 Temperature cutout switch
930 Thermocouple temperature sensing transducer
940 Implant heating electrode with thermocouple
950 Implant heating electrode
960 Thermocouple leads to temperature cutout switch

DESCRIPTION OF THE PREFERRED EMBODIMENT

Figure 1:
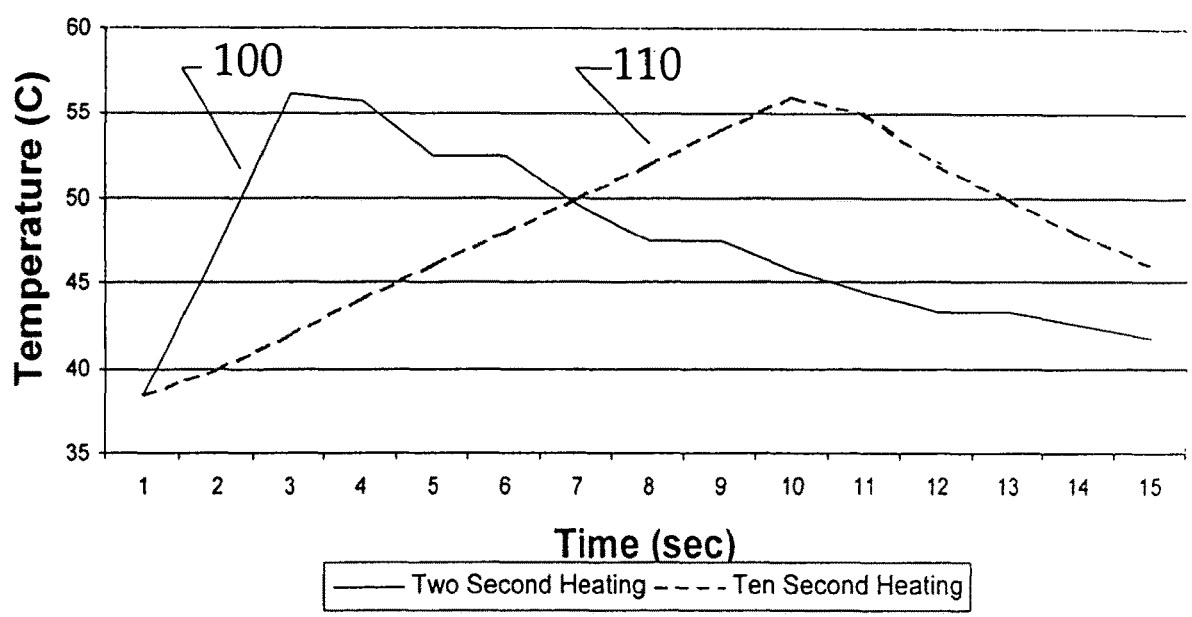
FIG. 1 Memory metal implant temperature versus heating duration curve
Figure 2:
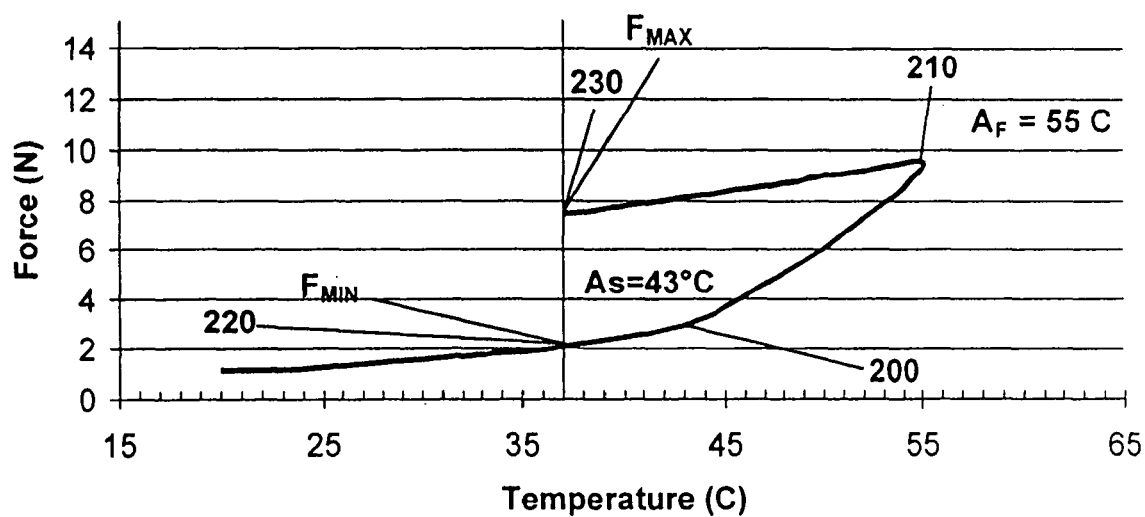
FIG. 2 Implant tissue force versus implant temperature curve
Figure 3:
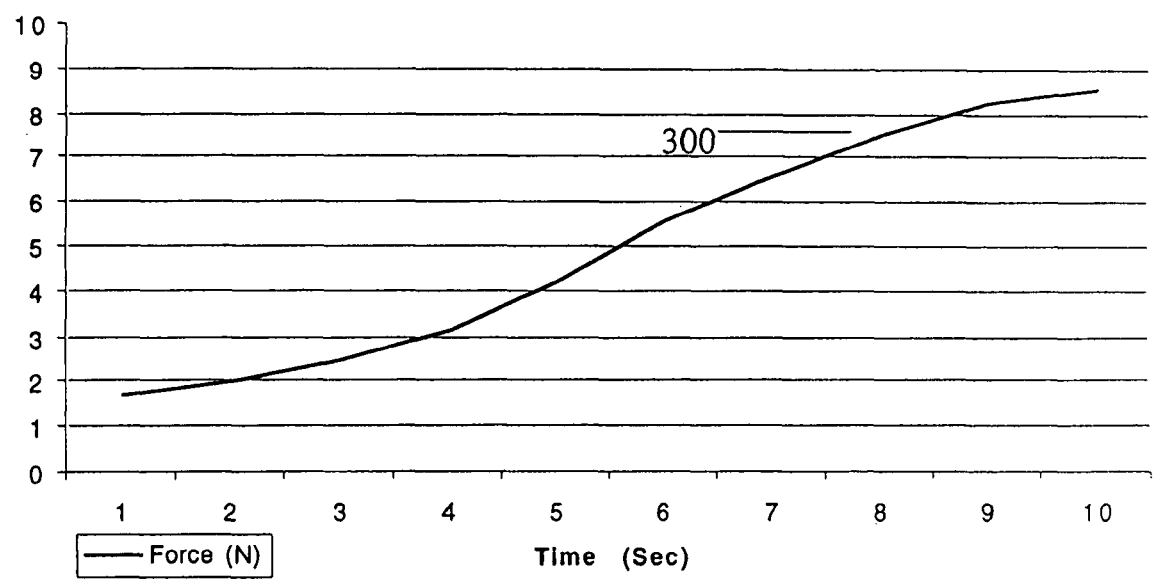
FIG. 3 Implant tissue force versus shape change period curve

The preferred embodiment of the invention consists of an electronic control console that operates using a lookup table, algorithm or mathematical model to control the temperature of a memory ahoy implant in such a manner so as to control the extent of its transformation from a martensitic to austenitic microstructure. The rate of heat application controls the rate of implant shape change (FIG. 1). Rapid heating curves (100) and slow controlled heating curves (110) both can provide sufficient heat energy to fully convert the material's phase and shape. The magnitude of heat transferred controls the state-of-the-metal's phase change thus the force exerted on surrounding tissue (FIG. 2). Force and temperature relationships exist for each shape-changing element of an implant. In an implant restrained in bone the force exerted by the implant increases with temperature. The tissue force begins at or near the austinetic start temperature [$A_s$] (200) and increases until the austinetic finish temperature [$A_f$] (210) as shown in the implant temperature versus force curve (FIG. 2). The force can be controlled from a minimum value of the force at body temperature [$F_{min}$] (220) before heating and at body temperature after heating [$F_{max}$] (230). With these relationships for a given implant shape-changing member and power setting, a force versus time curve will exist (FIG. 3). Consequently, a force versus power curve will exist for any shape-changing member at a constant heating period.

Figure 4:
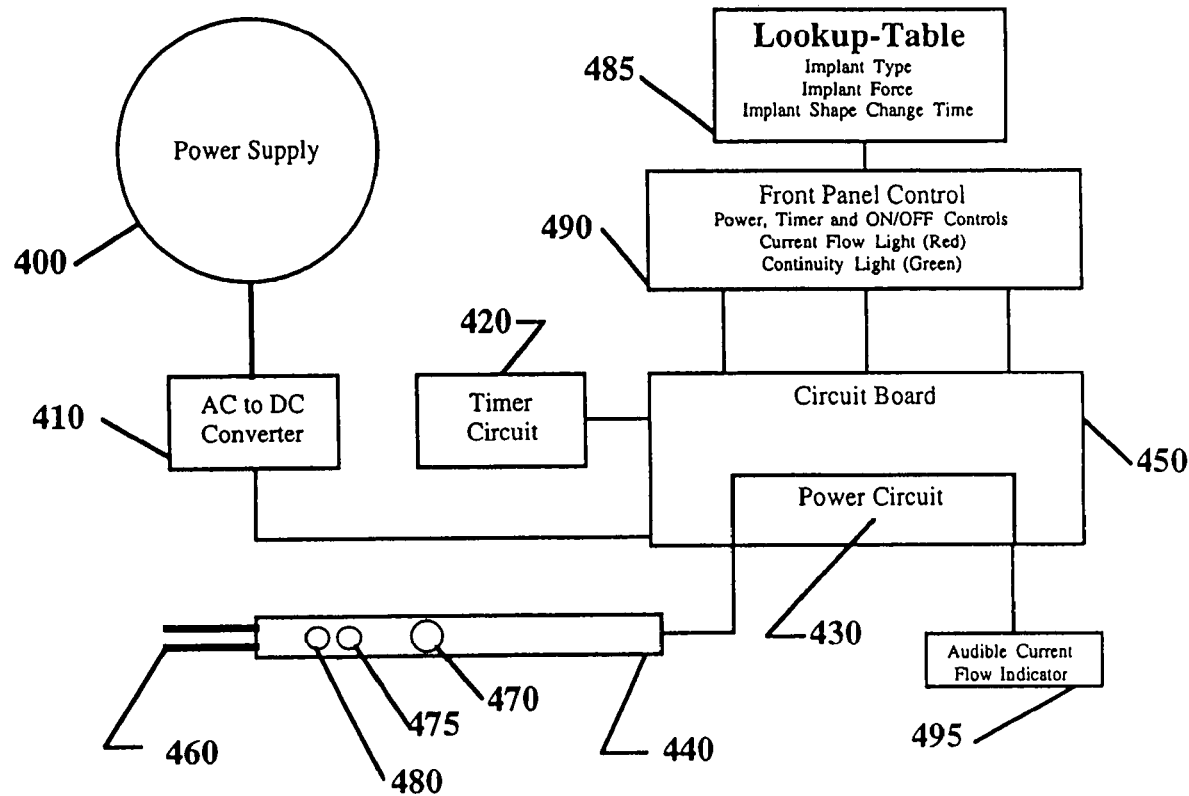
FIG. 4 System diagram based on lookup table

The control of the heat energy to the implant is implemented using a device: having a power supply with electrical patient isolation transformer (400), rectifying circuit to convert alternating to direct current (410), user controllable timing circuit (420), user controllable power circuit (430), a user operated current delivery electrode (440), circuit board (450), bipolar current delivery electrode (460), heating control button (470), implant-system continuity light (475), implant-system heat energy light (480), lookup table (485), front control panel with time, power, on-off switch, and indicator lights (490), and an audible operational indicator (495) (FIG. 4). The lookup table (485) could be in the form of an alphanumeric table, mathematical model, or algorithm.

The primary data from the surgeon consists of the 1) the implant selected, 2) the period of which the implant should change shape, and 3) the percentage of the total force available in this style of implant to be applied to the surrounding tissue. Each implant has a separate lookup table (500) (FIG. 5). This table can be within an operator's manual or embedded in the instrument.

The rate data, time for the implant to close, is used as row (510) or column (520) headings and the force is the alternate column heading. The voltage setting to achieve the desired implant result is read from within the cells (530) of the table.

Operation of the Invention

In the operation of the preferred embodiment, the surgeon will select the implant to be used; maximum level of force for the implant to apply to the surrounding tissue, and the amount of time that the implant should take to change shape. Other variables such as ambient temperature of the implant, amount of bone movement expected, and extent of shape change when correcting bone angulation can also be inputted or listed in the lookup table (485).

Once the instrument is connected to a source of electricity so as to energize the power supply (400), the surgeon after review of the lookup table (485) sets the controls on the front panel of the instrument (490). After placing the implant into bone the surgeon will bring the electrodes (460) into contact with the implant. The electrodes (460) when touching the implant cause the continuity light (475) to illuminate to show the surgeon that the force and rate control system is in optimal contact with the implant to deliver a user selected amount of heat energy over a user specified period of time. The surgeon then applies heat energy to the implant by actuating the heating control button (470). As the heating current flows the continuity light (475) turns off and the heat energy light (480) illuminates during the user-selected period for heat energy delivery. The front panel (490) time control knob sets the timing circuit (420) so as to control the rate of heat energy delivery and shape change period. Audible current flow indicator (495) assists the surgeon in the use of the system. The continuity light (475) and heat energy light (480) are located on the electrode handle (440) so as to be in clear view of the surgeon when working in the operative site. The circuit board (450) holds the electrical conductors, user controlled power circuit (430) and the other components required to complete the system.

If, as in most cases in bone fixation, the bony elements do not move in response to the force applied by the implant the force magnitude applied to tissue is as listed in the lookup table. If bone transport occurs then the force will be less than predicted. Under this condition the surgeon can measure the amount of bone transport, input these data into the lookup table and correct to obtain the actual applied force. This allows the surgeon to adjust the amount of displacement of bone as well as force exerted on bone during the implantation procedure. This provides fine control for the physician when stabilizing bone elements or fragments.

Once the heating energy is delivered the energy light (480) turns off and the cycle is complete. The heating energy can be applied multiple times to the implant. In the condition of osteoporosis the surgeon may sequentially increase the closing force of the implant through stepping the closing force up at 10% to 20% increments until the surgeon receives operative clues that the maximum implant fixation force has been applied without causing fracture of the osteoporotic bone. The subject invention for the first time gives full control to the physician to provide a plurality of implant force and closing rate characteristics to each of plurality of implant designs.

Description of the First Alternate Embodiment

The first alternate embodiment of the invention is based on the same principals of the preferred embodiment which controls the conversion of the martensitic to austenitic phase transition of the implant material. This first alternate embodiment integrates elements such as but not limited to a lookup table, algorithms, heat transfer models of the implants (640) and predictive graphics model of the shape change of the implant and force applied to the tissue. These image and numeric data are displayed on the front panel (630) monitor and controlled using the front panel (630) keyboard to allow the surgeon to observe the theoretical effects of heating to the implant and adjust the heat energy to the implant to get the desired clinical effect.

In this embodiment the power supply (600), AC to DC converter (610), and circuit board (655) are configured to support a microprocessor (650) and computer memory which contains model data, model algorithms, and lookup tables (640) to allow the modeling of the effects of heat energy application to the implant. This intelligent system front panel (630) displays implant images, shape change data, and allows the model predictions of the rate and force of implant shape change to be compared to the operative observations. The timer relay (620) and power circuit (670) in this embodiment are microprocessor (650) controlled. An audible current flow indicator (660) and combined continuity and heat energy light (690), in addition to the front panel (630) enhance surgeon feedback to the operation of the subject invention in this embodiment. In this configuration the surgeon will program the force and rate profile and then using the electrode handle (680) place the electrodes (695) on the point of the implant shown on the front panel (630) monitor to apply heat. Once the electrode (695) is in contact with the element of the implant the electrode start button (685) is pushed, the front panel (630) monitor then displays the theoretical effect on the implant and directs the surgeon to the next element of the implant for heat energy application.

Operation of the First Alternate Embodiment of the Invention

This first alternate embodiment allows the surgeon to predict the changes to the implant and then observe the in vivo effects of the implant on bony elements. These features increase the feedback to the surgeon, compensate for and controls heating of multiple elements of an implant and enhances the degree of force and rate control of the implant for the surgeon.

In use the surgeon will select and display the implant on the front panel (630) monitor. Then the desired rate and tissue force will be input by the surgeon, using the front panel (630) for each shape-changing element incorporated into the implant. Once set the front panel (630) monitor will guide the surgeon in using the electrode handle (680). The monitor will display the point of contact for the electrode (695) and instruct the surgeon to actuate the electrode start button (685). The monitor will then display the theoretical shape change and tissue force and guide the surgeon to place the electrode handle (680) on the next shape-changing member of the implant.

Figure 8:
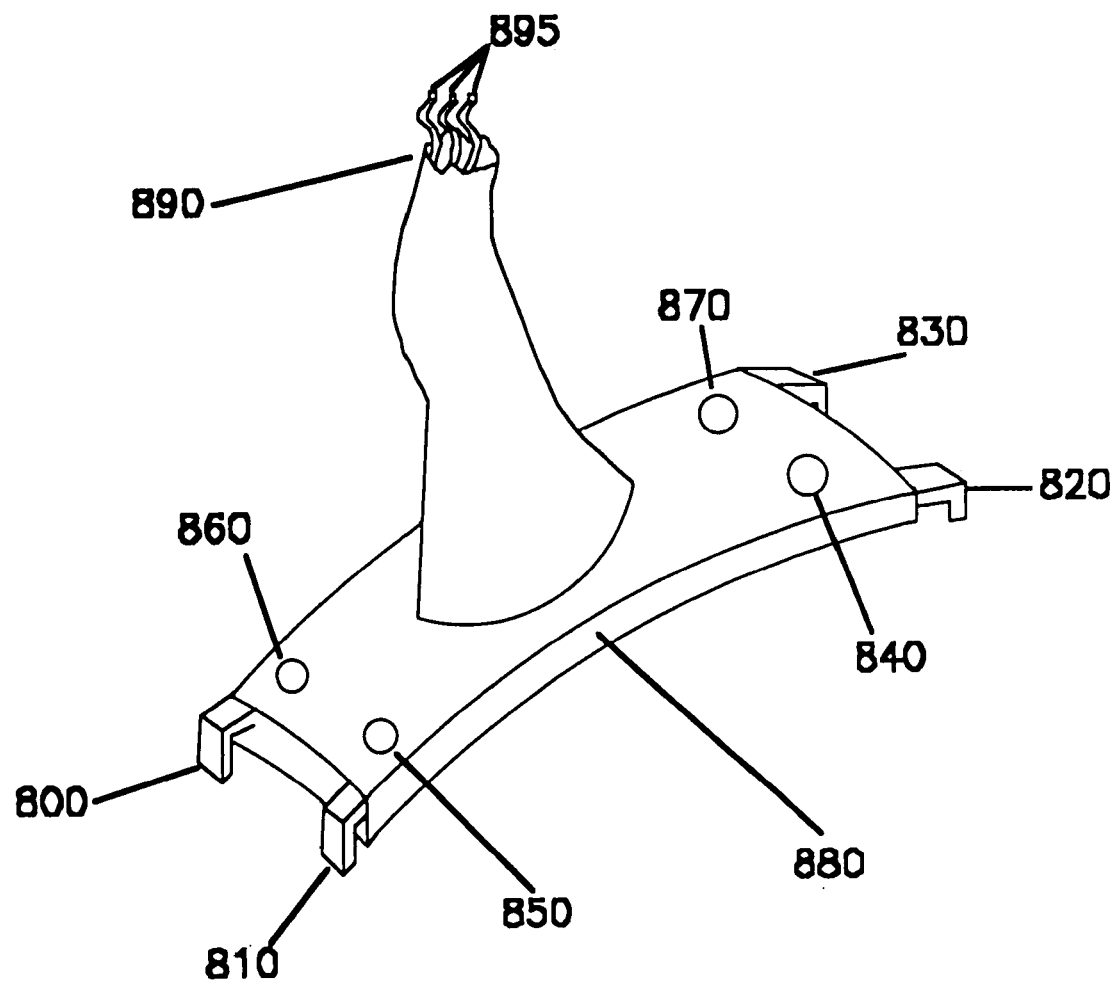
FIG. 8 Multi-element implant electrode example

As shown in the spinal plate of FIG. 7 multiple shape changing members may need to be controlled. Members that lock into bone (720, 730, 740, and 750) or shrink to shorten the plant (705 and 710) can be selectively controlled. In FIG. 7 member 720 can be affected by applying current to circular points 760 and 765. Member 750 can be affected by applying heat energy to points 780 and 785. And length shortening or angle changing member 710 can be affected by applying heating energy across "x" marked points 770 and 775. A single bipolar electrode can be used at multiple locations to close each shape-changing member one at a time. Alternatively a multi-electrode handle FIG. 8 can be placed on the implant and the subject invention can then heat each implant shape changing element (FIG. 7) in the selected sequence. In this manner electrode handle 880 can heat the shape-changing member 720 by having the electrode handle apply current to electrode points 830 and 870. Or member 705 of FIG. 7 can be shortened or lengthened by applying heat energy with the handle (880) and electrodes 840 and 850.

During the process the surgeon can adjust the force applied to the tissue, correct for bone transport that may make the force estimate inaccurate and then instruct the surgeon when the implant is in its final configuration.

Description of the Second Alternate Embodiment

In the second alternate embodiment the implant-heating model and lookup table are replaced with a measurement of the implant temperature. This temperature measurement is taken from the surface of the implant. Temperature measurement devices include but are not limited to thermocouples and thermal imaging. Other feedback mechanisms such as strain gauges that measure the shape change of the implant can be used for feedback control. These measured data are input to the model or a switch that stops current flow to the implant.

Figure 6:
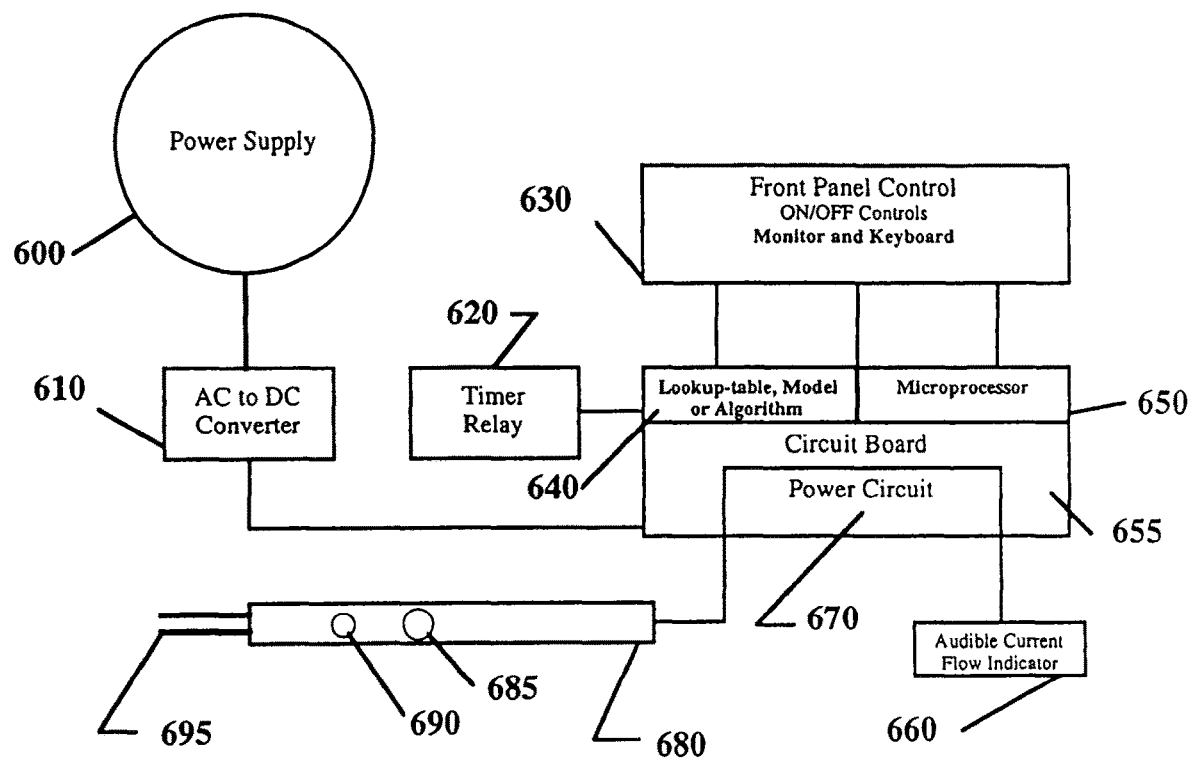
FIG. 6 System diagram based on models, algorithms and lookup tables

The system diagram of FIG. 6 now takes data from the heat sensing transducers to input into the algorithm and implant models (640) so that the microprocessor (650) can correlate force and rate data with temperature and accurately control the implant's shape change. This method accounts for the environmental temperature issues associated with a cold operating room and a warm patient.

Figure 9:
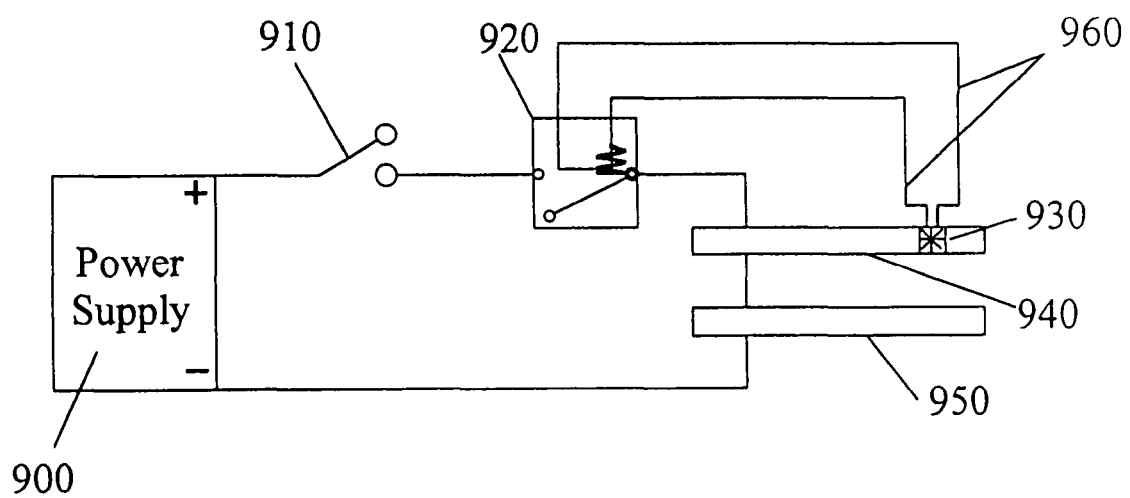
FIG. 9 Electrode handle and system circuit diagram for simple feedback and control system example

The FIG. 9 system diagram illustrates the temperature feedback embodiment of the invention. Here the power supply (900) is connected to the user-actuated electrode start button (910) which provides power to a current cutout switch (920) that receives input from the thermocouple (930), located on the electrode (940), through the thermocouple wires (960). The electrode (950) could hold an additional thermocouple for product redundancy and additional points of temperature measurement.

Operation of the Second Alternate Embodiment of the Invention

In this embodiment the amount of power set on the power supply (900) will control the rate of heating and the setting for the cutout switch (920) is related to the force. In the simple configuration of FIG. 9 a lookup table is used to set the power level and the cutout parameters.

In use the surgeon selects these two parameters and the system automatically cuts out at the implant temperature corresponding to a specific tissue force.

Conclusions, Ramifications and Scope of the Invention

The reader will see that the system and method described in the specifications to control the rate, displacement and force of a shape changing implant provides an important modality for the surgeon in the treatment of skeletal injury and disease.

While the above description is specific this should not be construed as limitations of the scope of the invention, but rather as an example of a plurality of possible embodiments which exhibit the characteristics of controlling implants formed from shape memory material. Thus any system that individually or in concert controls the rate, displacement and force exerted on tissue by a shape memory material implant is within the scope and spirit of this invention.

Accordingly, the scope of the invention should be determined not by the embodiments illustrated, but by the appended claims and their legal equivalents.

What is claimed:
1. A method comprising:
(a) selecting an implant comprising a memory material having a shape changing transition temperature range that has a shape that is designed to be controlled with an energy delivery device, wherein
(i) the memory material comprises martensitic phase memory material,
(ii) the martensitic phase memory material is operable to transition to austenitic phase memory material in the shape changing transition temperature range, and
(iii) the step of selecting the implant is based, at least in part, on a maximum level of force the implant can apply when changed in shape;
(b) implanting the implant during a surgical procedure;
(c) utilizing the energy delivery device to deliver an amount of energy to change the shape of the implant by transitioning at least some of the martensitic phase memory material to the austenitic phase memory material, wherein

(i) the amount of energy delivered by the energy deliver device is selected to change the shape of the implant to a selected shape having a selected amount of force from a plurality of pre-selected increments of energy that correspond to a plurality of incremental shape changing forces that change the shape of the implant to a corresponding plurality of incremental shape change positions,
(ii) the corresponding plurality of incremental shape change positions are positions of the implant that successively further change the shape of the implant, and
(iii) the energy delivery device is used to control (A) the rate of change in the shape of the implant and (B) the amount of energy delivered by the energy delivery device to the implant.

2. The method of claim 1, wherein the implant is selected from the group consisting of catheters, intrauterine contraceptive devices, gastrointestinal compression clip, blood vessel filter, coronary artery stent, skin staple, bone staple, and bone plate.

3. The method of claim 1, wherein the implant comprises a plurality of members, wherein the plurality of members are operable to be controlled together by the energy delivery device.

4. The method of claim 1, wherein the implant comprises a plurality of members, wherein the plurality of members are operable to be controlled independently by the energy delivery device.

5. The method of claim 1, wherein the memory material has martensitic to austenitic finish transition temperatures sufficiently different so that the plurality of incremental shape change positions can be implemented so as to achieve high resolution control of a characteristic selected from the group consisting of an implant force, rate of shape change, extent of shape change.

6. The method of claim 1, wherein the change in the shape of the implant is opening or closing of the implant.

7. The method of claim 1, wherein the plurality of the pre-selected increments are pre-selected to control a pre-selected characteristic selected from the group consisting of (a) a corresponding plurality of incremental shape change forces, (b) a corresponding plurality of periods of time of incremental rate of shape change of the implant, (c) a corresponding plurality of extents of shape change of the implant, and (d) combinations thereof.

8. The method of claim 7, wherein the pre-selected characteristic comprises a combination of (a) the corresponding plurality of the incremental shape change forces, (b) the corresponding plurality of the periods of time of the incremental rate of shape change of the implant, and (c) the corresponding plurality of the extents of shape change of the implant.

9. The method of claim 7, wherein the pre-selected characteristic comprises the corresponding plurality of the incremental shape change forces.

10. The method of claim 9, wherein the corresponding plurality of the incremental shape change forces are incrementally between 10% and 20% increments of the maximum level of force.

11. The method of claim 9, wherein the corresponding plurality of the incremental shape change forces are 10%, 20%, 30%, 40%, 50%, 60%, 70%, 80%, 90%, and 100% of the maximum level of force.

12. The method of claim 9, wherein the pre-selected characteristic further comprises the corresponding plurality of the periods of time of the incremental rate of shape change of the implant.

13. The method of claim 9, wherein the pre-selected characteristic further comprises the corresponding plurality of the extents of shape change of the implant.

14. The method of claim 7, wherein the pre-selected characteristic comprises the corresponding plurality of the periods of time of the incremental rate of shape change of the implant.

15. The method of claim 14, wherein the corresponding plurality of the periods of time of the incremental rate of shape change of the implant are incrementally one second increments.

16. The method of claim 14, wherein the pre-selected characteristic further comprises the corresponding plurality of the extents of shape change of the implant.

17. The method of claim 7, wherein the pre-selected characteristic comprises the corresponding plurality of the extents of shape change of the implant.

18. The method of claim 17, wherein the corresponding plurality of the extents of shape change of the implants are incrementally between 10% and 20% increments.

19. The method of claim 17, wherein the corresponding plurality of the extents of shape change of the implant are 10%, 20%, 30%, 40%, 50%, 60%, 70%, 80%, 90%, and 100%.

20. The method of claim 1, wherein the implant is operable to be being controlled with the energy delivery device using a feedback control loop.

21. The method of claim 20, wherein the feedback control loop measures temperature of the implant.

* * * * *